United States Patent [19]

Takematsu et al.

[11] Patent Number: 4,824,477
[45] Date of Patent: * Apr. 25, 1989

[54] TRIFLUOROMETHANESULFONANILIDE COMPOUNDS AND HERBICIDAL COMPOSITIONS CONTAINING THEM

[75] Inventors: Tetsuo Takematsu; Makoto Konnai, both of Utsunomiya; Kuniaki Shimizu, Shimizu; Ikumi Urushibata; Ikuo Kajiwara, both of Shizuoka, all of Japan

[73] Assignees: Kumiai Chemical Industry Co., Ltd.; Ihara Chemical Industry Co., Ltd., both of Tokyo, Japan

[ * ] Notice: The portion of the term of this patent subsequent to Apr. 21, 2004 has been disclaimed.

[21] Appl. No.: 19,331

[22] Filed: Feb. 26, 1987

Related U.S. Application Data

[63] Continuation-in-part of Ser. No. 871,870, Jun. 9, 1986, Pat. No. 4,659,371.

[30] Foreign Application Priority Data

Jun. 11, 1985 [JP] Japan .................... 60-125228

[51] Int. Cl.$^4$ .................. A01N 41/06; C07C 143/74
[52] U.S. Cl. ..................... 71/103; 558/408; 558/426
[58] Field of Search ............. 71/103; 558/408, 426

[56] References Cited

U.S. PATENT DOCUMENTS 3,639,474 2/1972 Harrington et al. ............ 71/103
4,659,371 4/1987 Takematsu et al. ............ 71/103

Primary Examiner—Mary C. Lee
Assistant Examiner—Zinna Northington
Attorney, Agent, or Firm—Oblon, Fisher, Spivak, McClelland & Maier

[57] ABSTRACT

A trifluoromethanesulfonanilide compound having the formula:

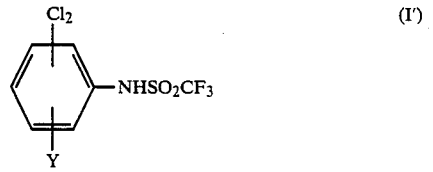

wherein Y is a (1-cyano-2-propyl)cyclopropyl group or a (1-cyano)cyclopentyl group.

6 Claims, No Drawings

TRIFLUOROMETHANESULFONANILIDE COMPOUNDS AND HERBICIDAL COMPOSITIONS CONTAINING THEM

This is a continuation-in-part application of Ser. No. 871,870, filed on June 9, 1986, now U.S. Pat. No. 4,659,371.

BACKGROUND OF THE INVENTION

1. Field of the Invention

The present invention relates to novel trifluoromethanesulfonanilide compounds and herbicidal compositions containing them as active ingredients.

2. Discussion of Background

In recent years, many herbicides have been developed and practically used, and they have contributed to the saving of the labor force for the agricultural work and to the improvement of the productivity.

However, in the practical use, these herbicides have various problems in respect of the herbicidal activities and safety, and development of further improved herbicides is desired.

U.S. Pat. No. 3,639,474 discloses that certain trifluoromethanesulfonanilide compounds have herbicidal activities. However, the compounds disclosed in this U.S. patent have drawbacks that their herbicidal activities are rather poor against perennial weeds, and further their safety against cotton is rather low.

SUMMARY OF THE INVENTION

The present inventors have conducted extensive researches to solve such problems, and as a result, have found that the trifluoromethanesulfonanilide compounds of the formula I as defined hereinafter exhibit excellent herbicidal effects against perennial weeds such as Johnsongrass (*Sorghum halepense*) and purple nutsedge (*Cyperus rotundus*) and superior safety against cotton, as compared with the compounds disclosed in the above-mentioned U.S. patent, and they have a high level of safety also against a sunflower (*Helianthus annuus*). The present invention has been accomplished on the basis of this discovery.

The patent application Ser. No. 871,870 is directed to a trifluoromethanesulfonanilide compound having the formula:

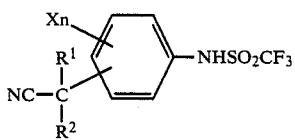

wherein each of $R^1$ and $R^2$ is a lower alkyl group, X is a halogen atom or a trifluoromethyl group, n is an integer of 0 to 2, and $R^1$ and $R^2$ may form, together with the adjacent carbon atom, a ring which may be substituted by a lower alkyl group.

The compound of the formula I can be prepared by reacting an aniline derivative having the formula:

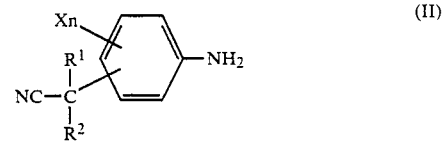

wherein $R^1$, $R^2$, X and n are as defined above, with trifluoromethanesulfonic acid anhydride or a trifluoromethanesulfonic acid halide.

The present invention provides a trifluoromethanesulfonanilide compound having the formula:

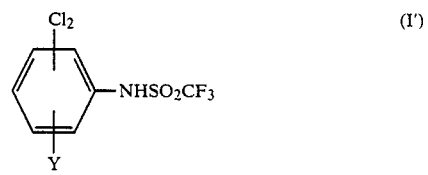

wherein Y is a (1-cyano-2-propyl)cyclopropyl group or a (1-cyano)cyclopentyl group.

More specifically, the present invention is directed to a trifluoromethanesulfonanilide compound having the formula:

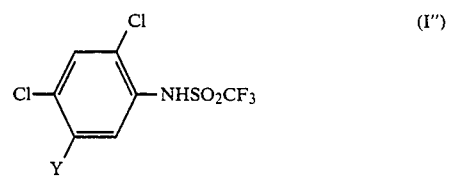

wherein Y is a (1-cyano-2-propyl)cyclopropyl group or a (1-cyano)cyclopentyl group.

The compounds of the formulas I' and I'' may be prepared in the same manner as the preparation of the compound of the formula I.

The present invention also provides a herbicidal composition comprising a herbicidally effective amount of the compound of the formula I' and an agricultural adjuvant.

Further, the present invention provides a method for killing weeds which comprises applying a herbicidally effective amount of the compound of the formula I to a locus to be protected.

DETAILED DESCRIPTION OF THE PREFERRED EMBODIMENTS

In the formulas I and II, each of $R^1$ and $R^2$ is a lower alkyl group, preferably a methyl group or an ethyl group. Otherwise, $R^1$ and $R^2$ may form, together with the adjacent carbon atom, a ring which may be substituted by a lower alkyl group, such as a cyclopropyl group, a cyclopentyl group, a methylcyclopropyl group or an ethylcyclopropyl group.

X is a halogen atom such as a chlorine atom or a fluorine atom, or a trifluoromethyl group.

Specific examples of the compounds of the formula I will be presented in Table 1. The compound numbers will be referred to in the subsequent description.

TABLE 1

$$\text{X}_n\text{-C}_6\text{H}_3(\text{Y})\text{-NHSO}_2\text{CF}_3$$

| Compound No. | Xn | Y | Melting point (°C.) Boiling point (°C./mmHg), or Refractive index ($n_D^{20}$) |
|---|---|---|---|
| 1 | H | 4-C(CH₃)₂-CN | mp 118–120 |
| 2 | 2-Cl | 4-C(CH₃)₂-CN | mp 92–93 |
| 3 | 3-Cl | 4-C(CH₃)₂-CN | mp 140–142 |
| 4 | 2-CF₃ | 4-C(CH₃)₂-CN | mp 133–137 |
| 5 | 2-Cl | 5-C(CH₃)₂-CN | bp 122–126/0.025 ri 1.4951 |
| 6 | 2,4-Cl₂ | 5-C(CH₃)₂-CN | mp 115–116 |
| 7 | 2-F, 4-Cl | 5-C(CH₃)₂-CN | mp 131–133 |
| 8 | 2,4-F₂ | 5-C(CH₃)₂-CN | mp 112–113 |
| 9 | H | 4-C(C₂H₅)₂-CN | mp 104–105 |
| 10 | H | 4-(cyclopropyl)-CN | mp 128–130 |
| 11 | H | 4-(cyclopentyl)-CN | mp 133–135 |
| 12 | 2-Cl | 4-(cyclopropyl)-CN | mp 88–93 |
| 13 | 2-Cl | 5-(cyclopropyl)-CN | mp 115–118 |
| 14 | 2-F | 5-(cyclopropyl)-CN | mp 99–103 |

TABLE 1-continued

[Structure: Xn, Y-substituted phenyl-NHSO₂CF₃]

| Compound No. | Xn | Y | Melting point (°C.) Boiling point (°C./mmHg), or Refractive index ($n_D^{20}$) |
|---|---|---|---|
| 15 | 2,4-Cl₂ | 5-(cyclopropyl)-CN | mp 168–169 |
| 16 | 2,4-Cl₂ | 5-(cyclopropyl with CH₃)-CN | mp 161–163 |
| 17 | 4-Cl | 3-C(CH₃)₂-CN | mp 113–119 |
| 18 | 2,5-Cl₂ | 4-C(CH₃)₂-CN | ri 1.5219 |
| 19 | 3-Cl | 4-(cyclopropyl)-CN | mp 112–114 |
| 20 | 2,4-Cl₂ | 5-(cyclopropyl with C₂H₅)-CN | mp 152–155 |
| 21 | 2,4-Cl₂ | 5-(cyclopropyl with C₃H₇-n)-CN | mp 124–127 |
| 22 | 2,4-Cl₂ | 5-(cyclopentyl)-CN | mp 87.5–88 |

The compounds of the present invention represented by the formula I can be prepared by a process which comprises reacting an aniline derivative of the formula II with trifluoromethanesulfonic acid anhydride or a trifluoromethanesulfonic acid halide in the presence or absence of a solvent such as acetone, methyl ethyl ketone, dimethylformamide, dimethylsulfoxide, tetrahydrofuran, benzene, toluene, xylene, chlorobenzene, chloroform, dichloromethane or carbon tetrachloride, in the presence or absence of an organic or inorganic base, for example, an alkali metal carbonate such as sodium hydroxide, potassium carbonate or sodium hydrogen carbonate or a tertiary amine such as triethylamine, dimethylaniline or pyridine, at a temperature of from −15° to 100° C. for from 1 to 20 hours.

Now, the process for the production of the compounds of the present invention will be described in detail with reference to Examples.

PRODUCTION EXAMPLE 1 (COMPOUND NO. 5)

Production of 2-chloro-5-(1-cyano-1-methyl)-ethyltrifluoromethanesulfonanilide

Into a 100 ml reaction flask equipped with a thermometer, a dropping funnel and a nitrogen supply tube, 2.9 g (0.015 mol) of 2-chloro-5-(1-cyano-1-methyl) ethylaniline, 1.5 g (0.015 mol) of triethylamine and 50 ml of dichloromethane were introduced, and 5.0 g (0.018 mol) of trifluoromethanesulfonic acid anhydride was gradually dropwise added under nitrogen pressure at 0° C. under stirring. After the completion of the dropwise addition, the stirring was continued at room temperature for 3 hours. The reaction solution was washed three times with 30 ml of 10% hydrochloric acid and further with water, and then dried over anhydrous sodium sulfate. The solvent was distilled off under reduced pressure. The residue thus obtained was distilled under reduced pressure to obtain 3.5 g of 2-chloro-5-(1-cyano-1-methyl) ethyl trifluoromethanesulfonanilide as a light yellow transparent viscous liquid of a fraction having a boiling point of from 122° to 126° C./0.025 mmHg. The refractive index $N_D^{20}$ was 1.4951.

PRODUCTION EXAMPLE 2 (COMPOUND NO. 10)

Production of 4-(1-cyano)cyclopropyltrifluoromethane sulfonanilide

Into a 100 ml reaction flask equipped with a thermometer, a dropping funnel and a nitrogen supply tube, 3.1 g (0.02 mol) of (1-cyano)cyclopropylaniline, 1.7 g (0.022 mol) of pyridine and 50 ml of dichloromethane were introduced, and 6.2 g (0.022 mol) of trifluoromethanesulfonic acid anhydride was gradually dropwise added under nitrogen pressure at 0° C. under stirring. After the completion of the dropwise addition, the stirring was continued at room temperature for 4 hours. The reaction solution was washed three times with 30 ml of 10% hydrochloric acid and further with water, and dried over anhydrous sodium sulfate. The solvent was distilled off under reduced pressure. The crude crystals thus obtained were recrystallized from ethanol to obtain 4.8 g of 4-(1-cyano)cyclopropyltrifluoromethanesulfonanilide as a yellow brown powder having a melting point of from 128° to 130° C.

PRODUCTION EXAMPLE 3 (COMPOUND NO. 15)

Production of 2,4-dichloro-5-(1-cyano)cyclopropyl trifluoromethanesulfonanilide

Into a 100 ml reaction flask equipped with a thermometer, a dropping funnel and a nitrogen supply tube, 2.7 g (0.012 mol) of 2,4-dichloro-5-(1-cyano) cyclopropylaniline, 1.3 g (0.013 mol) of triethylamine and 50 ml of dichloromethane were introduced, and 3.7 g (0.013 mol) of trifluoromethanesulfonic acid anhydride was gradually dropwise added under nitrogen pressure at 0° C. under stirring. After the completion of the dropwise addition, the stirring was continued at room temperature for 4 hours. The reaction solution was washed three times with 30 ml of 10% hydrochloric acid and further with water, and dried over anhydrous sodium sulfate. The solvent was distilled off under reduced pressure. The crude crystals thus obtained was washed with n-hexane to obtain 2.6 g of 2,4-dichloro-5-(1-cyano)cyclopropyltrifluoromethanesulfonanilide as colorless crystals having a melting point of from 168° to 169° C.

Compound Nos. 1 to 4, 6 to 9, 11 to 14 and 16 to 20 were prepared in the manners similar to the above Examples.

PRODUCTION EXAMPLE 4 (COMPOUND NO. 22)

Production of 2,4-dichloro-5-(1-cyano)cyclopentyl trifluoromethanesulfonanilide

Into a 100 ml reaction flask equipped with a thermometer, a dropping funnel and a nitrogen supply tube, 3.8 g (0.015 mol) of 2,4-dichloro-5-(1-cyano) cyclopentylaniline, 2.0 g (0.02 mol) of triethylamine and 50 ml of dichloromethane mol) of trifluoromethanesulfonic acid anhydride was gradually dropwise added under nitrogen pressure at 0° C. under stirring. After the completion of the dropwise addition, the stirring was continued at room temperature for 3 hours. The reaction solution was washed three times with 30 ml of 10% hydrochloric acid and further with water, and dried over anhydrous sodium sulfate. The solvent was distilled off under reduced pressure. The crude crystals thus obtained was recrystallized from ethanol to obtain 1.8 g of 2,4-dichloro-5-(1-cyano)cyclopentyltrifluoromethanesulfonanilide as colorless crystals having a melting point of from 87.5° to 88° C.

PRODUCTION EXAMPLE 5 (COMPOUND NO. 21)

Production of 2,4-dichloro-5-(1-cyano-2-propyl)cyclopropyl trifluoromethanesulfonanilide Into a 100 ml reaction flask equipped with a thermometer, a dropping funnel and a nitrogen supply tube, 4.0 g (0.015 mol) of 2,4-dichloro-5-(1-cyano-2-propyl)-cyclopropylaniline, 2.0 g (0.02 mol) of triethylamine and 50 ml of dichloromethane were introduced, and 5.6 g (0.02 mol) of trifluoromethanesulfonic acid anhydride was gradually dropwise added under nitrogen pressure at 0° C. under stirring. After the completion of the dropwise addition, the stirring was continued at room temperature for 4 hours. The reaction solution was washed three times with 30 ml of 10% hydrochloric acid and further with water, and dried over anhydrous sodium sulfate. The solvent was distilled off under reduced pressure. The crude crystals thus obtained was washed with n-hexane to obtain 1.3 g of 2,4-dichloro-5-(1-cyano-2-propyl)cyclopropyltrifluoromethanesulfonanilide as yellow crystals having a melting point of from 124° to 127° C.

The compounds of the present invention may be used as herbicides by themselves or in combination with agricultural adjuvants such as a carrier, a surface active agent, a dispersant, an assisting agent, etc. in the form of various formulations such as wettable powders, granules, emulsifiable concentrates or dusts.

As the carrier used for the formulation, there may be mentioned a solid carrier such as talc, bentonite, clay, kaoline, diatomaceous earth, white carbon, vermiculite, slaked lime, silica, ammonium sulfate or urea, or a liquid carrier such as isopropylalcohol, xylene or cyclohexane. As the surface active agent and dispersant, there may be mentioned, for instance, a sulfate of an alcohol, an alkyl sulfonate, a lignin sulfonate, a polyoxyethylene glycol ether, a polyoxyethylene alkyl aryl ether, or a polyoxyethylene sorbitan monoalkylate. As the assisting agent, for instance, carboxymethyl cellulose, polyethylene glycol or gum arabic may be mentioned. In the actual application, the herbicidal composition may be applied directly or after being diluted to a proper concentration.

Now, Formulation Examples for the herbicidal composition of the present invention will be described. However, it should be understood that the present invention is by no means restricted to these specific Examples.

FORMULATION EXAMPLE 1 (GRANULES)

10% by weight of Compound No. 1, 2% by weight of sodium salt of a lauryl alcohol sulfuric acid ester, 5% by weight of sodium lignin sulfonate, 2% by weight of carboxymethyl cellulose and 81% by weight of clay were uniformly mixed and pulverized. To 80 parts by weight of this mixture, 20 parts by weight of water was added, and the mixture was kneaded. The kneaded mixture was granulated by an extrusion type granulating machine and dried to obtain granules of from 14 to 32 mesh.

TABLE 1-continued $$Xn \underset{Y}{\underset{|}{\bigcirc}} -NHSO_2CF_3$$

| Compound No. | Xn | Y | Melting point (°C.) Boiling point (°C./mmHg), or Refractive index ($n_D^{20}$) |
|---|---|---|---|
| 15 | 2,4-Cl$_2$ | 5-△-CN | mp 168–169 |
| 16 | 2,4-Cl$_2$ | 5-△(CH$_3$)-CN | mp 161–163 |
| 17 | 4-Cl | 3-C(CH$_3$)$_2$-CN | mp 113–119 |
| 18 | 2,5-Cl$_2$ | 4-C(CH$_3$)$_2$-CN | ri 1.5219 |
| 19 | 3-Cl | 4-△-CN | mp 112–114 |
| 20 | 2,4-Cl$_2$ | 5-△(C$_2$H$_5$)-CN | mp 152–155 |
| 21 | 2,4-Cl$_2$ | 5-△(C$_3$H$_7$-n)-CN | mp 124–127 |
| 22 | 2,4-Cl$_2$ | 5-⬠-CN | mp 87.5–88 |

The compounds of the present invention represented by the formula I can be prepared by a process which comprises reacting an aniline derivative of the formula II with trifluoromethanesulfonic acid anhydride or a trifluoromethanesulfonic acid halide in the presence or absence of a solvent such as acetone, methyl ethyl ketone, dimethylformamide, dimethylsulfoxide, tetrahydrofuran, benzene, toluene, xylene, chlorobenzene, chloroform, dichloromethane or carbon tetrachloride, in the presence or absence of an organic or inorganic base, for example, an alkali metal carbonate such as sodium hydroxide, potassium carbonate or sodium hydrogen carbonate or a tertiary amine such as triethylamine, dimethylaniline or pyridine, at a temperature of from −15° to 100° C. for from 1 to 20 hours.

Now, the process for the production of the compounds of the present invention will be described in detail with reference to Examples.

PRODUCTION EXAMPLE 1 (COMPOUND NO. 5)

Production of 2-chloro-5-(1-cyano-1-methyl)-ethyltrifluoromethanesulfonanilide

Into a 100 ml reaction flask equipped with a thermometer, a dropping funnel and a nitrogen supply tube, 2.9 g (0.015 mol) of 2-chloro-5-(1-cyano-1-methyl) ethylaniline, 1.5 g (0.015 mol) of triethylamine and 50 ml of dichloromethane were introduced, and 5.0 g (0.018 mol) of trifluoromethanesulfonic acid anhydride was gradually dropwise added under nitrogen pressure at 0° C. under stirring. After the completion of the dropwise addition, the stirring was continued at room temperature for 3 hours. The reaction solution was washed three times with 30 ml of 10% hydrochloric acid and further with water, and then dried over anhydrous sodium sulfate. The solvent was distilled off under reduced pressure. The residue thus obtained was distilled under reduced pressure to obtain 3.5 g of 2-chloro-5-(1-cyano-1-methyl) ethyl trifluoromethanesulfonanilide as a light yellow transparent viscous liquid of a fraction having a boiling point of from 122° to 126° C./0.025 mmHg. The refractive index $N_D^{20}$ was 1.4951.

PRODUCTION EXAMPLE 2 (COMPOUND NO. 10)

Production of 4-(1-cyano)cyclopropyltrifluoromethane sulfonanilide

Into a 100 ml reaction flask equipped with a thermometer, a dropping funnel and a nitrogen supply tube, 3.1 g (0.02 mol) of (1-cyano)cyclopropylaniline, 1.7 g (0.022 mol) of pyridine and 50 ml of dichloromethane were introduced, and 6.2 g (0.022 mol) of trifluoromethanesulfonic acid anhydride was gradually dropwise added under nitrogen pressure at 0° C. under stirring. After the completion of the dropwise addition, the stirring was continued at room temperature for 4 hours. The reaction solution was washed three times with 30 ml of 10% hydrochloric acid and further with water, and dried over anhydrous sodium sulfate. The solvent was distilled off under reduced pressure. The crude crystals thus obtained were recrystallized from ethanol to obtain 4.8 g of 4-(1-cyano)cyclopropyltrifluoromethanesulfonanilide as a yellow brown powder having a melting point of from 128° to 130° C.

PRODUCTION EXAMPLE 3 (COMPOUND NO. 15)

Production of 2,4-dichloro-5-(1-cyano)cyclopropyl trifluoromethanesulfonanilide

Into a 100 ml reaction flask equipped with a thermometer, a dropping funnel and a nitrogen supply tube, 2.7 g (0.012 mol) of 2,4-dichloro-5-(1-cyano) cyclopropylaniline, 1.3 g (0.013 mol) of triethylamine and 50 ml of dichloromethane were introduced, and 3.7 g (0.013 mol) of trifluoromethanesulfonic acid anhydride was gradually dropwise added under nitrogen pressure at 0° C. under stirring. After the completion of the dropwise addition, the stirring was continued at room temperature for 4 hours. The reaction solution was washed three times with 30 ml of 10% hydrochloric acid and further with water, and dried over anhydrous sodium sulfate. The solvent was distilled off under reduced pressure. The crude crystals thus obtained was washed with n-hexane to obtain 2.6 g of 2,4-dichloro-5-(1-cyano)cyclopropyltrifluoromethanesulfonanilide as colorless crystals having a melting point of from 168° to 169° C.

Compound Nos. 1 to 4, 6 to 9, 11 to 14 and 16 to 20 were prepared in the manners similar to the above Examples.

PRODUCTION EXAMPLE 4 (COMPOUND NO. 22)

Production of 2,4-dichloro-5-(1-cyano)cyclopentyl trifluoromethanesulfonanilide

Into a 100 ml reaction flask equipped with a thermometer, a dropping funnel and a nitrogen supply tube, 3.8 g (0.015 mol) of 2,4-dichloro-5-(1-cyano) cyclopentylaniline, 2.0 g (0.02 mol) of triethylamine and 50 ml of dichloromethane mol) of trifluoromethanesulfonic acid anhydride was gradually dropwise added under nitrogen pressure at 0° C. under stirring. After the completion of the dropwise addition, the stirring was continued at room temperature for 3 hours. The reaction solution was washed three times with 30 ml of 10% hydrochloric acid and further with water, and dried over anhydrous sodium sulfate. The solvent was distilled off under reduced pressure. The crude crystals thus obtained was recrystallized from ethanol to obtain 1.8 g of 2,4-dichloro-5-(1-cyano)cyclopentyltrifluoromethanesulfonanilide as colorless crystals having a melting point of from 87.5° to 88° C.

PRODUCTION EXAMPLE 5 (COMPOUND NO. 21)

Production of 2,4-dichloro-5-(1-cyano-2-propyl)cyclopropyl trifluoromethanesulfonanilide Into a 100 ml reaction flask equipped with a thermometer, a dropping funnel and a nitrogen supply tube, 4.0 g (0.015 mol) of 2,4-dichloro-5-(1-cyano-2-propyl)-cyclopropylaniline, 2.0 g (0.02 mol) of triethylamine and 50 ml of dichloromethane were introduced, and 5.6 g (0.02 mol) of trifluoromethanesulfonic acid anhydride was gradually dropwise added under nitrogen pressure at 0° C. under stirring. After the completion of the dropwise addition, the stirring was continued at room temperature for 4 hours. The reaction solution was washed three times with 30 ml of 10% hydrochloric acid and further with water, and dried over anhydrous sodium sulfate. The solvent was distilled off under reduced pressure. The crude crystals thus obtained was washed with n-hexane to obtain 1.3 g of 2,4-dichloro-5-(1-cyano-2-propyl)cyclopropyltrifluoromethanesulfonanilide as yellow crystals having a melting point of from 124° to 127° C.

The compounds of the present invention may be used as herbicides by themselves or in combination with agricultural adjuvants such as a carrier, a surface active agent, a dispersant, an assisting agent, etc. in the form of various formulations such as wettable powders, granules, emulsifiable concentrates or dusts.

As the carrier used for the formulation, there may be mentioned a solid carrier such as talc, bentonite, clay, kaoline, diatomaceous earth, white carbon, vermiculite, slaked lime, silica, ammonium sulfate or urea, or a liquid carrier such as isopropylalcohol, xylene or cyclohexane. As the surface active agent and dispersant, there may be mentioned, for instance, a sulfate of an alcohol, an alkyl sulfonate, a lignin sulfonate, a polyoxyethylene glycol ether, a polyoxyethylene alkyl aryl ether, or a polyoxyethylene sorbitan monoalkylate. As the assisting agent, for instance, carboxymethyl cellulose, polyethylene glycol or gum arabic may be mentioned. In the actual application, the herbicidal composition may be applied directly or after being diluted to a proper concentration.

Now, Formulation Examples for the herbicidal composition of the present invention will be described. However, it should be understood that the present invention is by no means restricted to these specific Examples.

FORMULATION EXAMPLE 1 (GRANULES)

10% by weight of Compound No. 1, 2% by weight of sodium salt of a lauryl alcohol sulfuric acid ester, 5% by weight of sodium lignin sulfonate, 2% by weight of carboxymethyl cellulose and 81% by weight of clay were uniformly mixed and pulverized. To 80 parts by weight of this mixture, 20 parts by weight of water was added, and the mixture was kneaded. The kneaded mixture was granulated by an extrusion type granulating machine and dried to obtain granules of from 14 to 32 mesh.

TABLE 4-continued

| Tested compound | Dose of active ingredient (kg/ha) | Herbicidal index | | | | | |
|---|---|---|---|---|---|---|---|
| | | Sunflower | barnyard grass | Large crabgrass | Pig weed | Common black jack | Cocklebur |
| fluidone | 2 | 0 | 7 | 8 | 4 | 6 | 0 |

Note:
Perfluidone is a commercially available herbicide having the following chemical formula:

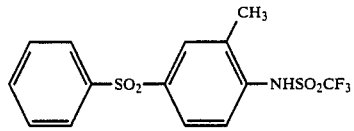

TEST EXAMPLE 4

A 600 cm² pot was filled with upland field soil, and seeds of barnyardgrass, large crab-grass, pig weed, lambsquater and flatsedge (*Cyperus iria*) were sown and covered with soil in a depth of from 0.5 to 1 cm. Then, a wettable powder prepared in accordance with Formulation Example 4, was diluted with 1 kl/ha of water and uniformly sprayed over the surface of soil at a dose of active ingredient of 1 kg/ha.

Twenty days after the treatment, the herbicidal effects were evaluated in accordance with the standards as identified in Test Example 1.

The results are shown in Tables 5 and 5'.

TABLE 5

| Tested compound | Herbicidal index | | | | |
|---|---|---|---|---|---|
| | Barnyardgrass | Large crabgrass | Pig weed | Lambsquater | Flatsedge |
| Compound 1 | 10 | 10 | 8 | 10 | 10 |
| Compound 2 | 10 | 10 | 10 | 10 | 10 |
| Compound 3 | 10 | 10 | 10 | 10 | 10 |
| Compound 4 | 10 | 10 | 10 | 10 | 10 |
| Compound 5 | 10 | 10 | 10 | 6 | 10 |
| Compound 6 | 10 | 10 | 10 | 8 | 10 |
| Compound 7 | 10 | 8 | 10 | 10 | 10 |
| Compound 8 | 10 | 6 | 10 | 10 | 10 |
| Compound 9 | 10 | 10 | — | — | 10 |
| Compound 10 | 10 | 10 | 8 | — | 10 |
| Compound 11 | 10 | 6 | — | — | 10 |
| Compound 12 | 10 | 6 | 10 | 8 | 10 |
| Compound 15 | 10 | 10 | 10 | 10 | 10 |
| Compound 16 | 10 | 10 | 10 | 10 | 10 |
| Compound 17 | 10 | 10 | 10 | 6 | 10 |
| Compound 18 | 10 | 10 | 10 | 8 | 10 |
| Compound 19 | 10 | 10 | 10 | 10 | 10 |
| Compound 20 | 10 | 10 | 9 | 8 | 10 |
| Comparative Compound 5 | 0 | 0 | 4 | 6 | 10 |
| Comparative Compound 6 | 0 | 0 | 2 | 10 | 10 |

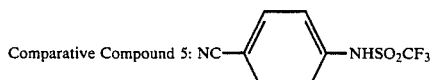

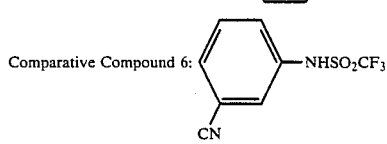

(Compounds disclosed in U.S. Pat. No. 3,639,474)

TABLE 5'

| Tested compound | Herbicidal index | | | | |
|---|---|---|---|---|---|
| | Barnyardgrass | Large crabgrass | Pig weed | Lambsquater | Flatsedge |
| Compound 22 | 10 | 10 | 10 | 8 | 10 |
| Comparative Compound 5 | 0 | 0 | 4 | 6 | 10 |
| Comparative Compound 6 | 0 | 0 | 3 | 10 | 10 |

TEST EXAMPLE 5

A 600 cm² pot was filled with upland field soil, and seeds of barnyardgrass, large crab-grass, pig weed, lambsquater and flatsedge were sown and covered with soil in a depth of from 0.5 to 1 cm.

When the barnyardgrass reached a 1-leaf stage, a wettable powder prepared in accordance with Formulation Example 4, was diluted with 1 kl/ha of water and uniformly sprayed over the surface of soil at a dose of the active ingredient of 4 kg/ha.

Fourteen days after the treatment, the herbicidal effects were evaluated in accordance with the standards as identified in Test Example 1.

The results are shown in Tables 6 and 6'.

TABLE 6

| Tested compound | Herbicidal index | | | | |
|---|---|---|---|---|---|
| | Barnyardgrass | Large crabgrass | Pig weed | Lambsquater | Flatsedge |
| Compound 1 | 10 | 10 | 10 | 10 | 10 |
| Compound 2 | 10 | 10 | 10 | 10 | 10 |
| Compound 3 | 10 | 8 | 10 | 10 | 10 |
| Compound 4 | 8 | 8 | 10 | 10 | 8 |
| Compound 5 | 10 | 8 | 10 | 10 | 10 |
| Compound 6 | 10 | 8 | 10 | 10 | 10 |
| Compound 7 | 7 | 8 | 10 | 10 | 10 |
| Compound 8 | 10 | 8 | 10 | 10 | 10 |
| Compound 9 | 4 | 7 | 10 | 10 | 10 |
| Compound 10 | 10 | 10 | 10 | 10 | 10 |
| Compound 11 | 7 | 7 | 8 | 10 | 10 |
| Compound 12 | 10 | 10 | 10 | 10 | 10 |
| Compound 13 | 10 | 10 | 8 | 10 | 10 |
| Compound 14 | 8 | 4 | 8 | — | 10 |
| Compound 15 | 8 | 10 | 10 | 10 | 10 |
| Compound 16 | 10 | 8 | 8 | 7 | 10 |
| Compound 17 | 10 | 8 | 10 | 10 | 10 |
| Compound 18 | 10 | 10 | 8 | 6 | 10 |
| Compound 19 | 10 | 10 | 10 | 10 | 10 |
| Compound 20 | 8 | 8 | 9 | 6 | 10 |
| Comparative Compound 5 | 2 | 4 | 10 | 10 | 10 |
| Comparative Compound 6 | 2 | 2 | 10 | 10 | 10 |

TABLE 6'

| Tested compound | Herbicidal index | | | | |
|---|---|---|---|---|---|
| | Barn-yard-grass | Large crab-grass | Pig weed | Lambs-quater | Flat-sedge |
| Compound 22 | 10 | 8 | 10 | 10 | 10 |
| Comparative Compound 5 | 2 | 4 | 10 | 10 | 10 |
| Comparative Compound 6 | 2 | 3 | 10 | 10 | 10 |

What is claimed is:

1. A trifluoromethanesulfonanilide compound having the formula:

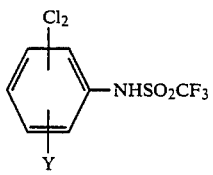

(I')

wherein Y is a (1-cyano-2-propyl)cyclopropyl group or a (1-cyano)cyclopentyl group.

2. A trifluoromethanesulfonanilide compound having the formula:

(I'')

wherein Y is a (1-cyano-2-propyl)cyclopropyl group or a (1-cyano)cyclopentyl group.

3. The compound according to claim 1, which is 2,4-dichloro-5-(1-cyano)cyclopentyltrifluoromethanesulfonanilide.

4. The compound according to claim 1, which is 2,4-dichloro-5-(1-cyano-2-propyl)cyclopropyltrifluoromethanesulfonanilide.

5. A herbicidal composition comprising a herbicidally effective amount of a compound of the formula I' as defined in claim 1 and an agricultural adjuvant.

6. A method for killing weeds, which comprises applying a herbicidally effective amount of a compound of the formula I' as defined in claim 1 to a locus to be protected.

* * * * *